United States Patent [19]

Beluzzi et al.

[11] 4,205,069

[45] May 27, 1980

[54] DIPEPTIDE NARCOTIC ANTAGONISTS

[75] Inventors: James D. Belluzzi, King of Prussia; William H. McGregor, Malvern; Larry Stein, Haverford, all of Pa.

[73] Assignee: American Home Products Corporation, New York, N.Y.

[21] Appl. No.: 947,276

[22] Filed: Sep. 29, 1978

[51] Int. Cl.² .................. A61K 37/00; C07C 103/52
[52] U.S. Cl. ........................... 424/177; 260/112.5 R
[58] Field of Search ................ 424/177; 260/112.5 R

[56] References Cited

U.S. PATENT DOCUMENTS 4,127,535  11/1978  Coy et al. ............................ 424/177

OTHER PUBLICATIONS

Pert et al., Nature 269, 73–75 (1977).
Janowsky et al., The Lancet, Aug. 5, 1978, pp. 320.

*Primary Examiner*—Delbert R. Phillips
*Attorney, Agent, or Firm*—Robert Wiser

[57] ABSTRACT

Novel dipeptides of the formula: A—X—Y—B wherein X is D-Tyr or L-Tyr; Y is D-Ala, L-Ala, D-Ser, L-Ser, or Gly; with the proviso that at least one of X and Y is of the D- configuration; A is hydrogen, allyl, or lower alkyl of 1 to 3 carbon atoms; B is —NH$_2$, —OMe, or —NHNH$_2$; and the pharmacologically acceptable salts thereof, as well as pharmaceutical compositions containing them, and a process for antagonizing the effects of a narcotic analgesic agent in warm blooded animals are disclosed.

5 Claims, No Drawings

DIPEPTIDE NARCOTIC ANTAGONISTS

BACKGROUND OF THE INVENTION

The problems associated with narcotic abuse and addiction and of the seemingly ubiquitous narcotics addict are very well known in today's society. Also well-known are the problems associated with curing an addict of his drug dependence. Because very often there is a psychological as well as a physiological dependence, the addict, once he has been withdrawn (cured) from his physiological drug dependence, will often return to narcotic usage for other, possible psychological, reasons. Thus a long term treatment and rehabilitation program for the narcotics addict has been suggested as being necessary (p. 259, A Goth, Medical Pharmacology, 2nd ed., C. V. Mosby, 1964). In addition, this long term program should allow the addict to otherwise function normally (i.e. attend school, maintain a job) during the ameliorative process. The drug, methadone, is today being utilized to aid in such long term treatment and rehabilitation programs.

A major problem associated with long term methadone therapy is the fact that the drug itself is an addicting narcotic with euphoriant properties; thus one is not curing addiction but merely making it less objectionable.

It is well-known (see for example, pp. 274-278, The Pharmacological Basis of Therapeutics, L. S. Goodman, and A. Gillman, Third ed., 1966, MacMillan), that certain agents (called narcotic antagonists) are able to prevent or abolish some or all of the clinical effects of a dose of a narcotic analgesic such as morphine or heroin in man and animals. Thus, for example, nalorphine prevents or abolishes, in appropriate species, narcotic induced euphoria, analgesia, drowsiness, respiratory depression and other well-known effects and side-effects associated with narcotic analgesic usage. Several narcotic antagonists are in use clinically, for example, to treat narcotic-induced respiratory depression. It is also known that in patients who are physically dependent on narcotic usage small doses of a narcotic antagonist, such as nalorphine, will precipitate acute withdrawal symptoms qualitatively identical to those seen after abrupt withdrawal of the narcotic agent. Thus, administration of the antagonist may be used as a simple, albeit unpleasant, method to test for physical dependence of the suspected narcotics addict.

Many reports in the recent literature (see for example, Agonist and Antagonist Actions of Narcotic Analgesic Drugs, H. W. Kosterlitz, H. O. J. Collier, and J. E. Fillarreal, editors, MacMillan, 1972, and references cited therein) propose the prophylactic use of a narcotic antagonist as an alternate medicinal approach to methadone therapy for the long term treatment and amelioration of narcotics addicts. Thus, it has been observed (M. Fink, A. M. Freedman, R. Resmick, and A. Zaks in Agonist and Antagonist Actions of Narcotic Analgesic Drugs, H. W. Kosterlitz, H. O. J. Collier, and J. E. Villarreal, editors, MacMillan, 1972) that when most previously detoxified narcotics addicts, who are receiving prophylactic therapy with a narcotic antagonist, are challenged with a narcotic agent they do not experience any of the expected clinical effects of the narcotic and their use of narcotic agents, in most cases, is eventually reduced.

In addition to the treatment of problems associated with narcotic analgesic abuse, narcotic analgesic antagonists have been indicated to be useful in the treatment of certain syndromes associated with mental disease or alcoholism, in particular catatonic stupor and hallucinations. See, for example, Emrich, Arzneim.Forsch./-Drug Research, 28 (II), Heft 8, 1271 (1978), and Schenk et al., Arzneim.-Forsch./Drug Res., 28, Heft 8, 1274 (1978).

SUMMARY OF THE INVENTION

The invention sought to be patented in a principal composition aspect resides in the concept of a compound of the formula:

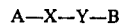

wherein X is D-Tyr or L-Tyr; Y is D-Ala, L-Ala, D-Ser, L-Ser, or Gly; with the proviso that at least one of X and Y is of the D-configuration; A is hydrogen, allyl, or lower alkyl of 1 to 3 carbon atoms; B is $-NH_2$, $-OMe$, or $NHNH_2$; and the pharmacologically acceptable salts thereof.

The tangible embodiments of the principal composition aspect of the invention possess the inherent general physical properties of being colorless to tan crystalline or amorphous solids, substantially soluble in water and methanol, and generally insoluble in organic solvents such as ether, benzene, hexane, and toluene.

The tangible embodiments of the principal composition aspect of the invention possess the inherent applied use characteristic of antagonizing the effects of narcotic analgesics in warm-blooded animals as evidenced by pharmacological evaluation according to standard test procedures. In addition, the dose needed to produce these desirable narcotic antagonizing effects has been demonstrated to elicit, at most, only minimal analgesic effects when evaluated by standard pharmacological test procedures. Further, the tangible embodiments of the principle composition aspect of the invention possess the inherent applied use characteristic of antagonizing the effects of enkephalin-like peptides in warmblooded animals as evidenced by pharmacological evaluation according to standard test procedures.

The compounds of this invention are therefore useful as antagonists in the treatment of acute narcotic analgesic poisoning. They also are useful in the treatment of compulsive narcotic abuse to antagonize the reinforcement of drug-seeking behavior and to prevent the development of physical dependence on addictive narcotic analgesics. These compounds are also useful as antagonists of both synthetic and naturally-occurring opioid peptides (endorphins and enkephalins). In this latter capacity they are useful to reduce excessive enkephalin and endorphin activity that has been associated with certain disease states such as hallucinations, and catatonic stupor associated with mental illness or alcoholism, as well as over-dosage with an enkephalin-like compound.

The invention sought to be patented in a subgeneric composition aspect resides in the concept of a compound of the principal composition aspect wherein Y is D-Ala or D-Ser.

The invention sought to be patented in a second composition aspect resides in the concept of a narcotic analgesic agent antagonist composition suitable for administration to a warm-blooded animal comprising:

(a) an amount, sufficient to elicit a narcotic antagonist response in a warm-blooded animal affected by a narcotic analgesic agent, of a compound of the formula:

A—X—Y—B wherein Y is D-Tyr or L-Tyr; Y is D-Ala, L-Ala, D-Ser, L-Ser, or Gly; A is hydrogen, allyl, or lower alkyl of 1 to 3 carbon atoms; B is —NH₂, —OMe, and —NHNH₂; and the pharmacologically acceptable salts thereof; and (b) a pharmaceutically acceptable carrier.

The invention sought to be patented in a principal process aspect resides in the concept of a process for antagonizing the effect of a narcotic analgesic agent in warm-blooded animals which comprises administering to a warm-blooded animal in need thereof a sufficient amount of a compound of the formula:

A—X—Y—B wherein X is D-Tyr or L-Tyr; Y is D-Ala, L-Ala, D-Ser, L-Ser, or Gly; A is hydrogen, allyl, or lower alkyl of 1 to 3 carbon atoms; B is —NH₂, —OMe, or —NHNH₂; and the pharmacologically acceptable salts thereof.

The invention sought to be patented in its first subgeneric process aspect resides in the concept of a process of the principal process aspect wherein Y is D-Ala or D-Ser.

The invention sought to be patented in a second process aspect resides in the concept of a process for alleviating hallucinations and catatonic stupor resulting from mental illness or alcoholism in a warm-blooded animal which comprises administering to a warm-blooded animal in need thereof, a sufficient amount of a compound of the formula:

A—X—Y—B wherein X is D-Tyr or L-Tyr; Y is D-Ala, L-Ala, D-Ser, L-Ser, or Gly; A is hydrogen, allyl, or lower alkyl of 1 to 3 carbon atoms; B is —NH₂, —OMe, or —NHNH₂; and the pharmacologically acceptable salts thereof.

The invention sought to be patented in a third process aspect resides in the concept of a process for antagonizing the effect of an enkephalin-like peptide in warm-blooded animals which comprises administering to a warm-blooded animal in need thereof, a sufficient amount of a compound of the formula:

A—X—Y—B wherein X is D-Tyr or L-Tye; Y is D-Ala, L-Ala, D-Ser, L-Ser, or Gly; A is hydrogen, allyl, or lower alkyl of 1 to 3 carbon atoms; B is —NH₂, —OMe, or —NHNH₂; and the pharmacologically acceptable salts thereof.

DETAILED SPECIFICATION

The dipeptides of the invention may be prepared either by classical peptide synthesis methods or by the well-known solid phase methodology. When classical methodology is used, the imidazole method (see page 16, Eberhard Schroder and Klaus Lubke, Methods of Peptide Synthesis, Volume 1, Academic Press, New York and London, 1965, hereinafter referred to in this specification as "The Peptides, Vol. 1") is conveniently employed for coupling of the appropriately protected amino acid, and deprotection is accomplished by either hydrogenation with 10% Pd on carbon (The Peptides, Vol. 1, pp. 26–27), trifluoroacetic acid, or hydrogen chloride in ethyl acetate (The Peptides, Vol. 1, p. 39).

When the peptides of the invention are prepared by solid phase methodology, diisopropyl carbodiimide and hydroxy benzotriazole are conveniently used for coupling, and 30% trifluoroacetic acid in methylene chloride may be used for removal of t-Boc; anhydrous hydrogen fluoride is suitable for complete deprotection and removal from resin. (See Stewart and Young, Solid Phase Peptide Synthesis, W. H. Freeman and Company, San Francisco, 1969).

Purification of the dipeptide product may be conveniently accomplished by column chromatography on Sephadex G-10, the elution being carried out with either 0.2 N or 20% acetic acid, depending on the solubility of the peptide.

More detailed description of the synthesis of a variety of the compounds of the invention is set forth below in the Examples. The other compounds of the invention are prepared by employing the appropriately blocked amino acids which are desired.

The pharmacologically acceptable salts of the polypeptides of this invention are acid addition salts in which the acid may be either organic or inorganic, as for example, hydrochloric, phosphoric, maleic, acetic, citric, succinic, malic, and the like. These salts are prepared and isolated by conventional methods.

In practicing the process aspects of the invention the instant compositions can be administered in a variety of dosage forms, both oral and parenteral. The dose requirements will vary with the particular composition being employed, the particular symptom or condition being treated, the severity of the symptoms being presented, and the animal being treated.

The dosage also varies with the size of the animal. In the case of a 70 kg. animal, when the compositions of the invention are employed to antagonize the effects of narcotic analgesic agents (other than in acute overdosage), to alleviate hallucinations or cationic stupor resulting from mental illness or alcoholism, or to antagonize the effects of enkephalin-like peptides, a dose of from about 2 to about 40 mg., and preferably from about 5 to 20 mg., is administered 1 to 3 times a day, preferably by the parenteral route. Preferably, therapy is initiated at lower dosages, the dose being thereafter increased until the desired effect is obtained. For treatment of acute narcotic overdosage, a single dose of from about 2 to about 10 mg. is administered, preferably by the intravenous route.

For unit dosages, the active ingredient can be compounded into any of the usual oral or parenteral dosage forms including tablets, capsules and liquid preparations such as elixirs and suspensions containing various coloring, flavoring, stabilizing and flavor masking substances. For compounding oral dosage forms the active ingredient can be diluted with various tableting materials such as starches of various types, calcium carbonate, lactose, sucrose and dicalcium phosphate to simplify the tableting and capsulating process. A minor proportion of magnesium stearate is useful as a lubricant. For compounding parenteral dosage forms the active ingredient can be suspended or dissolved in various isotonic media such as glucose or saline solution. In all cases, of course, the proportion of the active ingredient in said composition will be sufficient to impart narcotic antagonizing activity thereto.

As has been previously stated, the dose necessary to evoke antagonism to narcotic analgesic agents in warm-blooded animals has been observed to produce only minimal analgesic effects when tested in the same species of animal. This broad separation of narcotic antagonizing and analgesic effects is a desirable characteristic and is an additional benefit inuring to the practice of the instant invention. Thus, for example, a withdrawn narcotics addict receiving prophylactic therapy with a narcotic antagonist as taught by the instant invention would not be expected to experience any significant analgesia, ordinarily considered an undesirable unnecessary and unwanted side-effect of narcotic antagonist maintenance therapy.

Where used in this specification and claims, the terminology "antagonizing the effect of a narcotic analgesic agent" means:
1. the reversal of the clinical manifestations of a narcotic overdose, such as stupor and sedation; and
2. the elimination of the euphoriant and other effects of narcotic usage which are sought after by one who abuses narcotic drugs.

Where used in this specification and claims, the term "narcotic analgesic agent" is meant to include that well-known class of analgesic agents which produce narcosis and possess addiction liability, illustrative of which are such substances as morphine, codeine, heroin, meperidine, and hydromorphone. In medicine the members of this class are frequently called merely "narcotics" or "narcotic agents", and antagonists thereto are classified as "narcotic antagonists". However, certain non-analgesic compounds, such as the barbiturates, are sometimes said to possess narcotic properties. When one skilled in the art speaks of "narcotic antagonists" or antagonism to narcotic agents, one is not speaking with reference to such non-analgesic agents. The instant invention similarly is concerned only with the narcotic analgesic agents wherever reference is made to narcotics or narcotic agents or narcotic antagonists.

Where used in this specification and claims, the term "enkephalin-like peptides" means those peptide compounds both naturally occurring and synthetic, and of endogenous or exogenous origin, which exhibit the properties of producing analgesia upon administration to warm-blooded animals and of binding at opiate receptor sites of brain tissue of such animals, and comprising naturally occurring enkephalins and endorphins and synthetic analogs thereof. The enkephalin-like peptides are also known in the art as "opioid peptides".

The following examples further illustrate the best mode contemplated by the inventors for the practice of the invention.

EXAMPLE 1

Preparation of Carbobenzoxy-Tyr-(O-Benzyl)-D-Ala-Methyl Ester 16.2 G. (40 meq.) Z*-Tyr-(OBzl)-OH and 6.5 g. carbonyl diimidazole were combined in a minimum volume of tetrahydrofuran and allowed to react 2 hours at $T_R$. D-Ala-OMe-HCl (6.0 g.) and 6.0 ml. of triethylamine were added in DMF at 0° C. and the reaction mixture allowed to stir overnight while the ice melted. After removal of the solvent in vacuo the residue was taken up in ethyl acetate and washed with 5% $NaHSO_4$ and saturated $NaHCO_3$, filtered and the solvent removed in vacuo.

(*Z=carbobenzoxy).
TLC S. G. $CHCl_3$/MeOH 9:1 $R_F$ 0.85.

EXAMPLE 2

Preparation of Z-Tyr(OBzl)-D-Ala-$NH_2$

2 G. of the product of Example 1 were dissolved in 200 ml. of methanol, cooled to 0° C. and the solution saturated with ammonia. Ammonolysis was allowed to continue for 3 days at $T_R$ with stirring, when the colorless crystals were filtered, washed with methanol and dried in vacuo over KOH.
TLC S. C. $CHCl_3$/MeOH 9:1 detection $I_2$ $R_F$ 0.28.

EXAMPLE 3

H-Tyr-D-Ala-$NH_2$

1 G. of the product of Example 2 was hydrogenated in methanol at $T_R$ and 1 atmosphere with 600 mg. of 10% Pd. on carbon catalyst with a few drops of glacial acetic acid for 20 hours at $T_R$. The catalyst was removed by filtration and the methanol evaporated to dryness in vacuo. The product was lyophyllized from water to yield 500 mg. of title compound.
TLC S. C., BAW(UP), ninhydrin detection: $R_f$ 0.28.
150 Mg. of product was chromatographed on sephadex G-10 using 0.2 HOAC. 0.5 Ml. fractions were collected at a flow rate of 0.05 ml./min. and tubes 71–78 were combined and lyophyllized on the basis of TLC (S. G., BAW(UP) and ninhydrin detection. $R_F$ 0.23.
Amino Acid Analysis: Tyr, 1.04; Ala, 1.00; $NH_3$, 1.03.

EXAMPLE 4

1.2 G. of Z-Tyr-(OBzl)-D-Ala-OMe was hydrogenated in MeOH containing a few drops of glacial HOAC and 600 mg. of 10% Pd. on carbon for 20 hours at $T_R$ and 1 atmosphere. The catalyst was removed by filtration and the methanol evaporated to dryness in vacuo. The product was lyophyllized from water, 700 mg. being obtained.
150 Mg. of product was chromatographed on a column of sephadex G-10 using 0.2 N HOAC. 0.5 Ml. fractions were collected at a flow rate of 0.05 ml./min. and tubes 65–74 were combined and lyophyllized (107 mg.) on the basis of TLC (S. G. BAW(UP) and ninhydrin detection $R_F$ 0.39.
Amino Acid Analysis: Tyr, 1.02; Ala, 1.00.

EXAMPLE 5

Tyr-D-Ser-$NH_2$

D-Ser-(OBzl)-$NH_2$ was prepared from the t-Boc-Ser-(OBzl)-OH carbonyl diimidazole, and $NH_3$ (The Peptides, 1, p. 116). After removal of the t-Boc group with TFA, it was coupled with Z-Tyr-(OBzl)-imidazolide (see above reference). Deprotection of Z-Tyr-(OBzl)-D-Ser-(OBzl)-$NH_2$ was accomplished by hydrogenation in methanol using 10% Pd. on carbon as catalyst. The resulting dipeptide was purified by chromatography on Sephadex G-10 using 0.2 N HOAc.

EXAMPLE 6

H-D-Tyr-D-Ala-OMe t-Boc-D-Tyr-OH was coupled with D-Ala-OMe by the N-hydroxy-succinimide ester method (The Peptides, 1, p. 105). Deprotection was carried out using trifluoroacetic acid (The Peptides, 1, p. 39) and the resulting dipeptide methyl ester salt was purified by chromatography on Sephadex G-10 using 0.2 N HOAc.

EXAMPLE 7

H-Tyr-Ala-NH₂

This dipeptide was prepared in the manner described for Example 5 using t-Boc-L-Ala-OH, instead of the protected D-serine. The product was purified on Sephadex G-10 using 0.2 N HOAc.

EXAMPLE 8

H-Tyr-D-Met-NH₂

Prepared by solid phase using benzhydryl amine resin (14 g.) and t-Boc-D-Met-OH (10 g.) 5.4 g. hydroxybenzotriazole and 60 ml. DIC, deprotected with 30% TFA in MeCl₂ and coupled with 18 g. t-Boc di Cl Bzl-Tyr-OH and 5.4 g. hydroxybenzotriazole and 6.0 ml. DIC. Deprotection with HF in the presence of 10 ml. anisole. The dipeptide was purified on Sephadex G-10 using 0.2 N HOAc.

EXAMPLE 9

H-Tyr-D-Ala-NHNH₂

Clz-Tyr-(OBzl)-D-Ala-OMe (1.5 g.) was reacted with 1 ml. NH₂NH₂ in methanol at room temperature for 2 days with stirring. The solid was filtered acid washed with methanol. Clz-Tyr-(OBzl)-D-Ala-NHNH₂ (1.0 g.) was hydrogenated in MeOH containing 0.2 ml. of HOAc and 600 mg. of 10% Pd. on carbon overnight. The catalyst was filtered, the filtrate evaporated to dryness, and the residue triturated with Et₂O, dissolved in water and lyophyllized. 150 Mg. were purified by chromatography on Sephadex G-10 using 0.2 N HOAc. 77 mg.

EXAMPLE 10

Allyl-Tyr-D-Ala-OMe

533 Mg. (2 meq.) of H-Tyr-D-Ala-OMe in 80 ml. of methanol with 400 mg. (4 meq.) of powdered KHCl₃ and 484 mg. (4 meq.) of allyl bromide were refluxed 2.5 hours under nitrogen. The solution was evaporated to dryness and dried in vacuo over KOH. The desired product was purified by high performance liquid chromatography using reverse phase C-18 column and eluting with 0.1 molar NH₄OAc ph 4.2 containing 23% acetonitrile. The mass spectrometric analysis of the isolated product confirms the presence of an N-allyl group on the dipeptide. TLC (S. C., BAW peptidechlorine spray) indicated the presence of one major component $R_F$ 0.65.

EXAMPLE 11

Antagonism of Morphine-Induced Analgesia

The ability of a compound to antagonize the effects of a narcotic analgesic agent can be demonstrated by measuring the ability of a compound to decrease the duration of analgesia produced by a given dose of the narcotic analgesic agent. Duration of analgesia may conveniently be determined by testing for analgesia at regular intervals using a modification of the procedure of D'Amour and Smith, J. Pharmacol., 72, 74 (1941), the tail-flick test. In this test, the existence of analgesia in a rat is determined by measuring the increase in the latency period during which a rat will tolerate a high intensity light beam shining on the tip of its tail. The following data demonstrates antagonism to narcotic induced analgesia produced by compounds of the invention.

| | Results[a] | | |
|---|---|---|---|
| Test Compound | Dose (mg/kg., S.C.) | No. of Rats | Mean Duration of Analgesia[b] ± S.E.M. (minutes) |
| Morphine Sulfate (5 mg/kg., intraperitoneally) | | | |
| Control | — | 2 | 100.00 ± 20.00[c] |
| H-Tyr-D-Ala-NH₂ | 5 | 3 | 41.67 ± 3.33[d] |
| H-Tyr-D-Ala-O-Me | 2.5 | 2 | 37.50 ± 7.50[d] |
| | 5 | 2 | 27.50 ± 7.50[d] |
| Morphine Sulfate (2.5 mg/kg., subcutaneously) | | | |
| Control | — | 4 | 103.75 ± 9.437[e] |
| H-Tyr-D-Ala-NH₂ | 5 | 3 | 40.00 ± 10.408[d] |
| | 2.5 | 1 | 55.00 |
| | 1 | 1 | >90.00 |
| H-Tyr-D-Ala-O-Me | 5 | 3 | 61.67 ± 16.667[d] |
| | 2.5 | 1 | 45.00 |

[a]All rats were tested at 5-minute intervals in the tail-flick test until latencies of 2 to 5 sec. were obtained on three consecutive trials. All rats then received an injection of morphine sulfate (as indicated in the table) and were returned to the tail-flick test until three consecutive trials with no movement of the tail for 8 seconds were obtained. The rats then received a subcutaneous injection of the test compound, or a control injection, and were returned to the tail-flick test to determine the duration of analgesia.
[b]The duration score is the number of minutes the animal was completely analgesic (tail-flick latency >8 sec.) following injection of the test compound.
[c]One-way analysis of variance for all four groups: F = 9.970, df = (3,5), P = 0.15.
[d]Significantly different from vehicle control, P < .05, 1-tailed.
[e]One-way analysis of variance for 5 mg/kg. groups: F = 7.676, df = (2,7), P = .017.

EXAMPLE 12

| | Antagonism of Enkephalin Analog-Induced Analgesia Results[a] | | |
|---|---|---|---|
| Test Compound | Dose (mg/kg., S.C.) | No. of Rats | Mean Duration of Analgesia[b] ± S.E.M. (minutes) |
| Control | — | 4 | 50.0 ± 8.165 |
| H-Tyr-D-Ala-NH₂ | 5 | 5 | 31.0 ± 4.301[c] |
| H-Tyr-D-Ala-O-Me | 10 | 1 | 50.0 |
| | 5 | 1 | 5.0 |
| | 1.25 | 1 | 20.0 |

[a]The procedure is the same as in Example 11 except that analgesia was produced by an intraventricular injection of H-Tyr-D-Ala-Gly-Phe-D-Leu-NH₂, 1 μg. in 10 μl. of Ringers solution.
[b]The duration score was the same as in Table 1.
[c]Significantly different from vehicle control, P < .05, 1-tailed.

The subject matter which the applicants regard as their invention is particularly pointed out and distinctly claimed as follows:

1. A process for antagonizing the effect of a narcotic analgesic agent in warm-blooded animals which comprises administering to a warm-blooded animal in need thereof a sufficient amount of a compound of the formula:

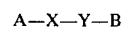

A—X—Y—B wherein X is D-Tyr or L-Tyr; Y is D-Ala; A is hydrogen, allyl, or lower alkyl of 1 to 3 carbon atoms; B is —NH₂, —OMe, or —NHNH₂; and the pharmacologically acceptable salts thereof.

2. The process according to claim 1 wherein the compound administered is D-Tyr-D-Ala-OMe.

3. The process according to claim 1 wherein the compound administered is L-Tyr-D-Ser-NH₂.

4. A process for antagonizing the effect of an enkephalin-like peptide in warm-blooded animals which comprises administering to a warm-blooded animal in need thereof a sufficient amount of a compound of the formula:

A—X—Y—B wherein X is D-Tyr or L-Tyr; Y is D-Ala; A is hydrogen, allyl, or lower alkyl of 1 to 3 carbon atoms; B is —NH$_2$, —OMe, or —NHNH$_2$; and the pharmacologically acceptable salts thereof.

5. The process according to claim 4 wherein the compound administered is D-Tyr-D-Ala-OMe.

* * * * *